United States Patent
Kubo et al.

(10) Patent No.: US 9,518,924 B2
(45) Date of Patent: Dec. 13, 2016

(54) FLUOROSCOPY APPARATUS AND FLUOROSCOPY APPARATUS OPERATING METHOD

(71) Applicant: OLYMPUS CORPORATION, Tokyo (JP)

(72) Inventors: Kei Kubo, Tokyo (JP); Yasushige Ishihara, Tokyo (JP); Hiromi Shida, Tokyo (JP); Satoshi Takekoshi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/499,813

(22) Filed: Sep. 29, 2014

(65) Prior Publication Data

US 2015/0016705 A1   Jan. 15, 2015

Related U.S. Application Data

(63) Continuation of application No. PCT/JP2013/059251, filed on Mar. 28, 2013.

(30) Foreign Application Priority Data

Apr. 4, 2012 (JP) ................................. 2012-085258

(51) Int. Cl.
  *G06K 9/00* (2006.01)
  *G01N 21/64* (2006.01)
  (Continued)

(52) U.S. Cl.
  CPC ......... *G01N 21/6456* (2013.01); *A61B 1/0005* (2013.01); *A61B 1/00009* (2013.01);
  (Continued)

(58) Field of Classification Search
  CPC .... A61B 1/00009; A61B 1/0005; A61B 1/043
  See application file for complete search history.

(56) References Cited

U.S. PATENT DOCUMENTS 4,349,255 A * 9/1982 Takayama ............. G01J 1/1626
  396/159
4,621,618 A * 11/1986 Omagari .................. A61B 1/12
  348/65
(Continued)

FOREIGN PATENT DOCUMENTS

JP   2006191989 A *  7/2006
JP   2010-172673 A    8/2010
(Continued)

OTHER PUBLICATIONS

International Search Report dated Jun. 18, 2013 issued in PCT/JP2013/059251.

*Primary Examiner* — Gandhi Thirugnanam
(74) *Attorney, Agent, or Firm* — Scully, Scott, Murphy & Presser, P.C.

(57) ABSTRACT

The invention provides a fluoroscopy apparatus including an image-capturing device that acquires a fluorescence image of a subject; a sensitivity adjusting portion that sets a sensitivity of the image-capturing device to fluorescence on the basis of a gradation value of the fluorescence image; a notifying portion that extracts a lesion part from the fluorescence image acquired by the image-capturing device with the sensitivity set by the sensitivity adjusting portion and presents it to an operator; and a display switching portion that displays the fluorescence image on a display unit when the sensitivity in the image-capturing device is equal to or less than a predetermined threshold and that presents information showing the existence of the lesion part on the notifying portion when the sensitivity is greater than the predetermined threshold.

4 Claims, 4 Drawing Sheets

(51) Int. Cl.
  *A61B 1/00* (2006.01)
  *A61B 1/04* (2006.01)
  *G06K 9/46* (2006.01)
  *G06T 7/00* (2006.01)
  *A61B 1/045* (2006.01)

(52) U.S. Cl.
  CPC .......... *A61B 1/00055* (2013.01); *A61B 1/043* (2013.01); *A61B 1/045* (2013.01); *G06K 9/4604* (2013.01); *G06T 7/0012* (2013.01); *F04C 2270/041* (2013.01); *G01N 2201/124* (2013.01); *G06T 2207/30004* (2013.01)

(56) References Cited

U.S. PATENT DOCUMENTS

| | | | | |
|---|---|---|---|---|
| 4,865,018 A * | 9/1989 | Kanno | ................ | H04N 17/002 348/72 |
| 5,769,789 A * | 6/1998 | Wang | .................... | G01R 33/28 382/131 |
| 6,333,971 B2 * | 12/2001 | McCrory | ...................... | 378/162 |
| 6,396,938 B1 * | 5/2002 | Tao | ...................... | G06K 9/2018 209/509 |
| 6,529,768 B1 * | 3/2003 | Hakamata | .......... | A61B 1/00009 600/310 |
| 7,235,045 B2 * | 6/2007 | Wang | ................ | A61B 1/00009 600/109 |
| 9,119,553 B2 * | 9/2015 | Ishihara | ............ | A61B 1/00009 |
| 2002/0168096 A1 * | 11/2002 | Hakamata | ................ | G06T 5/50 382/132 |
| 2005/0010081 A1 * | 1/2005 | Doguchi | ............ | A61B 1/00009 600/109 |
| 2006/0109460 A1 * | 5/2006 | Maeda | ................ | G01N 21/645 356/318 |
| 2010/0210903 A1 * | 8/2010 | Ishihara | ............ | A61B 1/00004 600/109 |
| 2010/0331624 A1 * | 12/2010 | Suzuki | ................ | A61B 1/0638 600/109 |
| 2012/0007001 A1 * | 1/2012 | Ishihara | ............ | A61B 1/00057 250/459.1 |
| 2012/0041250 A1 * | 2/2012 | Ishikawa | ................ | A61B 6/022 600/1 |
| 2012/0323072 A1 * | 12/2012 | Ishihara | ............ | A61B 1/00009 600/109 |
| 2012/0328175 A1 * | 12/2012 | Watanabe | .......... | A61B 1/00009 382/132 |
| 2013/0307952 A1 * | 11/2013 | Ishihara | ................ | A61B 1/043 348/68 |
| 2013/0314520 A1 * | 11/2013 | Ishihara | ................ | A61B 1/043 348/68 |
| 2014/0037179 A1 * | 2/2014 | Shida | .................. | A61B 5/0033 382/132 |
| 2015/0016705 A1 * | 1/2015 | Kubo | ................ | A61B 1/00009 382/132 |

FOREIGN PATENT DOCUMENTS

| | | | | |
|---|---|---|---|---|
| JP | WO 2012114934 A1 * | 8/2012 | ............ | A61B 1/043 |
| JP | EP 2656774 A1 * | 10/2013 | ............ | A61B 1/043 |
| JP | WO 2013150954 A1 * | 10/2013 | ......... | A61B 1/00009 |
| WO | WO 2011/118288 A1 | 9/2011 | | |

* cited by examiner

FLUOROSCOPY APPARATUS AND FLUOROSCOPY APPARATUS OPERATING METHOD

CROSS-REFERENCE TO RELATED APPLICATIONS

This is a continuation of International Application PCT/JP2013/059251, with an international filing date of Mar. 28, 2013, which is hereby incorporated by reference herein in its entirety. This application claims the benefit of Japanese Patent Application No. 2012-085258, filed on Apr. 4, 2012, the content of which is incorporated herein by reference.

TECHNICAL FIELD

The present invention relates to a fluoroscopy apparatus and to a fluoroscopy apparatus operating method.

BACKGROUND ART

In the related art, there are known endoscopes that irradiate a subject with excitation light that excites a fluorescent substance contained in the subject, that capture fluorescence coming from the subject, and that extract a lesion part from the fluorescence image (for example, see Patent Literature 1). Because the fluorescence image is an image in which a specific structure inside the subject is emphasized, it is easy to distinguish the lesion part.

CITATION LIST

Patent Literature

{PTL 1}
Japanese Unexamined Patent Application, Publication No. 2010-172673

SUMMARY OF INVENTION

A first aspect of the present invention is a fluoroscopy apparatus including an excitation light source that radiates excitation light onto a subject; a fluorescence-image acquisition portion including an image-capturing device that acquires a fluorescence image by capturing fluorescence generated in the subject by irradiating the subject with the excitation light from the excitation light source; a sensitivity adjusting portion that sets a sensitivity of the image-capturing device to fluorescence on the basis of a gradation value of the fluorescence image acquired by the image-capturing device; a notifying portion that extracts a region having a gradation value higher than a predetermined gradation threshold value from the fluorescence image acquired by the image-capturing device with the sensitivity set by the sensitivity adjusting portion and that presents information showing the existence of the extracted region to an operator; a display unit that displays the fluorescence image acquired by the image-capturing device; and a display switching portion that displays on the display unit the fluorescence image acquired by the image-capturing device when the sensitivity set in the image-capturing device by the sensitivity adjusting portion is equal to or less than a predetermined sensitivity threshold and that presents the information using the notifying portion when the sensitivity is greater than the predetermined sensitivity threshold.

A second aspect of the present invention is a fluoroscopy apparatus operating method for, on the basis of a gradation value of a fluorescence image of a subject acquired by an image-capturing device, adjusting the sensitivity of the image-capturing device to fluorescence, the fluoroscopy apparatus operating method including a displaying step of displaying the fluorescence image; a presenting step of presenting information showing the existence of a region having a gradation value greater than a predetermined gradation threshold value in the fluorescence image; and a switching step of selectively switching between the displaying step and the presenting step, wherein the switching step selects the displaying step when the sensitivity of the image-capturing device when the fluorescence image is acquired is less than or equal to a predetermined sensitivity threshold and selects the presenting step when the sensitivity is greater than the predetermined sensitivity threshold.

DESCRIPTION OF EMBODIMENT

A fluoroscopy apparatus 1 according to an embodiment of the present invention will be described below with reference to the drawings.

Figure 1:
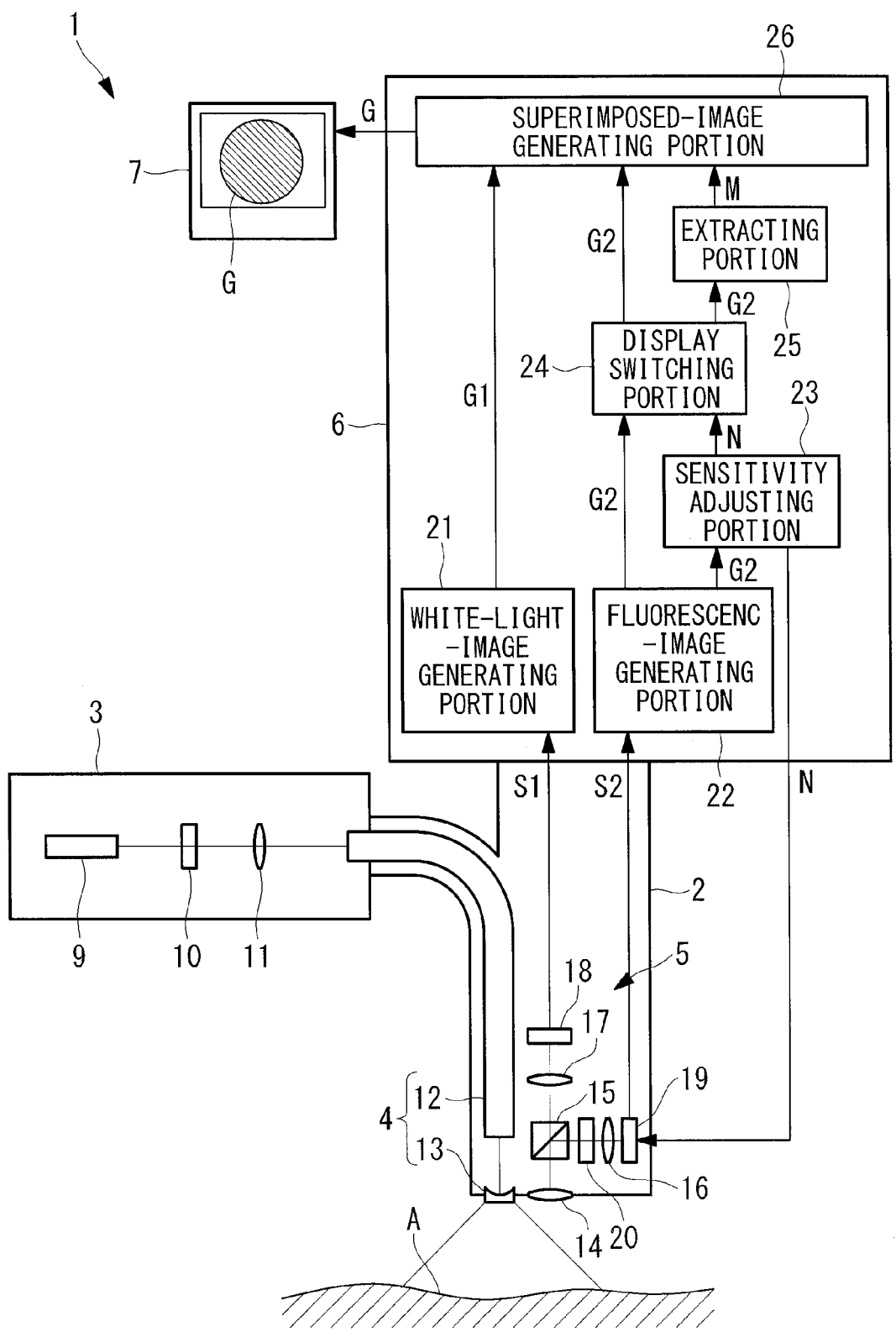
FIG. 1 is a diagram showing the overall structure of a fluoroscopy apparatus according to an embodiment of the present invention.

As shown in FIG. 1, the fluoroscopy apparatus 1 according to this embodiment includes an elongated inserted portion 2 that is inserted into a body, a light source (excitation light source, illumination light source) 3, an illumination unit 4 that radiates excitation light and illumination light coming from the light source 3 towards a subject A from the distal end of the inserted portion 2, an image-capturing unit 5 that is provided at the distal end of the inserted portion 2 and that acquires image information of the biological tissue serving as the subject A, an image processing unit 6 that is disposed at the proximal end of the inserted portion 2 and that processes the image information acquired by the image-capturing unit 5, and a display unit 7 that displays an image processed by the image processing unit 6.

The light source 3 is provided with a xenon lamp 9, a filter 10 that passes the excitation light and the illumination light (for example, in the wavelength band from 400 nm to 740 nm) from the light emitted from the xenon lamp 9, and a coupling lens 11 that condenses the excitation light and the illumination light passed by the filter 10.

The illumination unit 4 is provided with a light guide fiber 12 that is disposed along substantially the entire length of the inserted portion 2 in the longitudinal direction thereof and an illumination optical system 13 that is provided at the distal end of the inserted portion 2. The light guide fiber 12 guides the excitation light and the illumination light condensed by the coupling lens 11. The illumination optical system 13 expands the excitation light and the illumination light guided by the light guide fiber 12 to irradiate the subject A, which faces the distal end face of the inserted portion 2.

The image-capturing unit 5 includes an objective lens 14 that collects light coming from a prescribed observation region of the subject A; a dichroic mirror 15 that, of the light collected by the objective lens 14, reflects light with the excitation wavelength and above (excitation light and fluorescence) and transmits white light having a wavelength shorter than the excitation wavelength; two focusing lenses 16 and 17 that respectively focus the fluorescence reflected by the dichroic mirror 15 and the white light transmitted through the dichroic mirror 15; and two image-capturing devices (reference-image acquisition portion, fluorescence-image acquisition portion) 18 and 19, such as CMOS devices, that capture images of the white light and fluorescence focused by the focusing lenses 16 and 17. Reference sign 20 in the drawing is an excitation-light cut filter that blocks excitation light (for example, that transmits only light in the wavelength band from 760 nm to 850 nm) in the light reflected by the dichroic mirror 15.

The image processing unit 6 includes a white-light-image generating portion 21 that generates a white-light image (reference image) G1 from white-light-image information S1 acquired by the image-capturing device 18, a fluorescence-image generating portion 22 that generates a fluorescence image G2 from fluorescence-image information S2 acquired by the image-capturing device 19, a sensitivity adjusting portion 23 that adjusts the sensitivity of the image-capturing device 19 to the fluorescence, a display switching portion 24 that selectively switches the display mode according to the sensitivity set in the image-capturing device 19 by the sensitivity adjusting portion 23, an extracting portion (notifying portion) 25 that extracts a lesion part from the fluorescence image G2 and creates a marker M that indicates the position of the lesion part, and a superimposed-image generating portion 26 that generates a superimposed image G in which the fluorescence image G2 or the marker M created by the extracting portion 25 is superimposed on the white-light image G1.

The sensitivity adjusting portion 23 adjusts the image-capturing sensitivity of the image-capturing device 19 to the fluorescence by setting a binning pixel number N of the image-capturing device 19 on the basis of gradation values of the fluorescence image G2 generated by the fluorescence-image generating portion 22. More specifically, the sensitivity adjusting portion 23 calculates a representative value of the gradation values of the fluorescence image G2. The mean value or median value of the gradation values of all pixels in the fluorescence image G2 is used as the representative value. When the calculated representative value is smaller than a prescribed first threshold serving as a gradation threshold, the sensitivity adjusting portion 23 stepwise increases the binning pixel number N of the image-capturing device 19, for example, 2×2, 4×4, 8×8, . . . . On the other hand, when the calculated representative value is larger than a prescribed second threshold serving as a gradation threshold that is larger than the first threshold, the sensitivity adjusting portion 23 stepwise reduces the binning pixel number N of the image-capturing device 19, for example, 4×4, 2×2, 1×1.

The sensitivity adjusting portion 23 repeats the setting of the binning pixel number N in the image-capturing device 19 in this way every time the fluorescence image G2 is generated, so that the representative value of the gradation values of the fluorescence image G2 falls within a range between the first threshold value or greater and the second threshold value or less. When the binning pixel number N reaches a predetermined upper limit as a result of repeatedly increasing the binning pixel number N, the sensitivity adjusting portion 23 sets this upper limit in the image-capturing device 19.

The display switching portion 24 temporarily saves information about the binning pixel number N set in the image-capturing device 19 by the sensitivity adjusting portion 23 and selects either a "normal mode" or a "warning mode" as the display mode, depending on the binning pixel number N. Thus, the display switching portion 24 assigns the fluorescence image G2 captured by the image-capturing device 19 using the binning pixel number N and sent from the fluorescence-image generating portion 22 to the superimposed-image generating portion 26 or the extracting portion 25, depending on the selected display mode.

In other words, when the binning pixel number N is less than or equal to the predetermined threshold value set as the sensitivity threshold, the display switching portion 24 selects the "normal mode" and sends the fluorescence image G2 captured using that binning pixel number N to the superimposed-image generating portion 26. On the other hand, when the binning pixel number N is greater than the predetermined threshold value, the display switching portion 24 selects the "warning mode" and sends the fluorescence image G2 captured using that binning pixel number N to the extracting portion 25.

The sensitivity threshold of the binning pixel number N is set to, for example, 8×8. In other words, when the binning pixel number N is 8×8 or smaller (for example, 4×4), the "normal mode" is selected, whereas when the binning pixel number N is greater than 8×8, the "warning mode" is selected.

The fluorescence image G2 captured using that binning pixel number N is sent to the sensitivity adjusting portion 23. The sensitivity adjusting portion 23 newly sets the binning pixel number N on the basis of the gradation value of the fluorescence image G2 sent thereto and sends information about that binning pixel number N to the image-capturing device 19 and the display switching portion 24.

From the fluorescence image G2 sent from the display switching portion 24, the extracting portion 25 extracts a region having gradation values equal to or greater than a predetermined threshold as a lesion part. Then, the extracting portion 25 creates a marker M showing the position of the extracted lesion part. For example, an arrow indicating the lesion part, a circle surrounding the lesion part, or the like is used as the marker M.

Figure 2A:
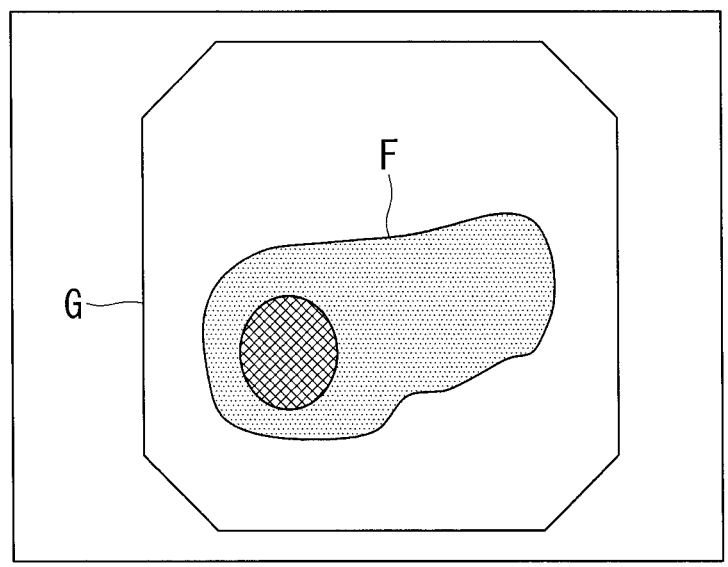
FIG. 2A is a diagram showing a superimposed image generated by the fluoroscopy apparatus in FIG. 1 in a normal mode.
Figure 2B:
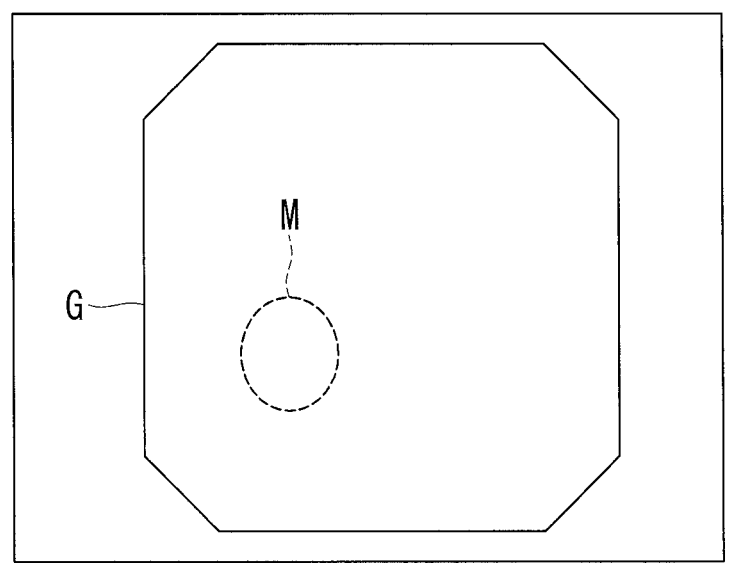
FIG. 2B is a diagram showing a superimposed image generated by the fluoroscopy apparatus in FIG. 1 in a warning mode.

The superimposed-image generating portion 26 superimposes the fluorescence image G2 sent from the display switching portion 24 or the marker M sent from the extracting portion 25 on the white-light image G1, thereby generating a superimposed image G, as shown in FIG. 2A and FIG. 2B. The superimposed-image generating portion 26 outputs the generated superimposed-image G to the display unit 7. In the superimposed image G, when the "normal mode" is selected, a fluorescence region F in the fluorescence image G2 is displayed, as shown in FIG. 2A, and when the "warning mode" is selected, the marker M is displayed, as shown in FIG. 2B. FIG. 2B illustrates an example in which a circle surrounding the lesion part is displayed as the marker M. The different hatching patterns in the fluorescence region F in FIG. 2A indicate differences in the fluorescence intensity, and the regions inside the hatching areas are regions where the fluorescence intensity is higher than in the region outside the hatching areas.

As for the fluorescence image G2 displayed in the superimposed image G when the "normal mode" is selected, a fluorescence image that is subjected to threshold processing in the display switching portion 24 for removing a background signal may be used.

Figure 3:
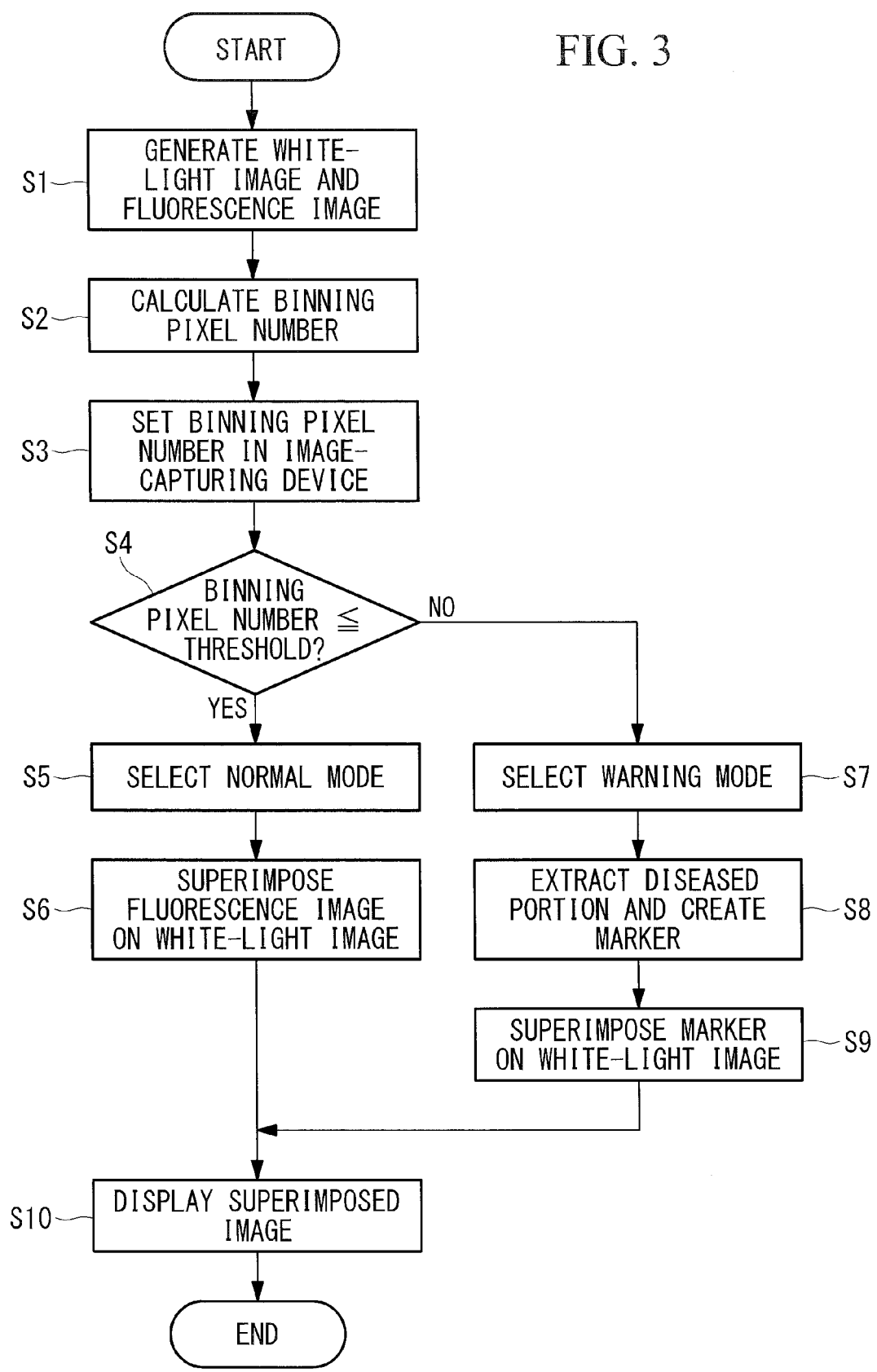
FIG. 3 is a flowchart showing the operation of the fluoroscopy apparatus in FIG. 1.

Next, the operation of the thus-configured fluoroscopy apparatus 1 according to this embodiment will be described with reference to FIG. 3.

To perform fluoroscopy using the fluoroscopy apparatus 1 according to this embodiment, illumination light and excitation light emitted from the light source 3 are guided to the distal end of the inserted portion 2 via the light guide fiber 12 and are expanded by the illumination optical system 13 so as to be radiated onto the subject A. By administering a fluorescent substance that preferentially accumulates in the lesion part to the subject A in advance, fluorescence is generated in the lesion part inside the subject A. In addition, the illumination light is reflected at the surface of the subject A.

After the fluorescence generated inside the subject A and the reflected illumination light reflected at the surface of the subject A are collected by the single objective lens 14, they are split into two by the dichroic mirror 15 and are captured by the two image-capturing devices 18 and 19. The white-light-image information S1 acquired by capturing the reflected light with the image-capturing device 18 is sent to the white-light-image generating portion 21 in the image processing unit 6, where the white-light image G1 is generated. On the other hand, the fluorescence-image information S2 acquired by capturing the fluorescence with the image-capturing device 19 is sent to the fluorescence-image generating portion 22 in the image processing unit 6, where the fluorescence image G2 is generated (step S1).

The generated fluorescence image G2 is sent to the sensitivity adjusting portion 23. The sensitivity adjusting portion 23 calculates the representative value of the gradation values of the fluorescence image G2, calculates the binning pixel number N so that the calculated representative value falls within a predetermined range (step S2), and sets the calculated binning pixel number N in the image-capturing device 19 (step S3). By doing so, the image-capturing sensitivity of the image-capturing device 19 is adjusted depending on the incident light level of the fluorescence on the image-capturing device 19, and the fluorescence generated in the subject A is thus reliably captured by the image-capturing device 19.

The binning pixel number N set in the image-capturing device 19 by the sensitivity adjusting portion 23 is sent to the display switching portion 24. When the binning pixel number N in the image-capturing device 19 is equal to or less than the predetermined threshold (YES in step S4, switching step), the display switching portion 24 selects the "normal mode" (step s5). Then, the superimposed-image generating portion 26 generates the superimposed image G in which the fluorescence image G2 sent from the display switching portion 24 is superimposed on the white-light image G1 (step S6) and outputs it to the display unit 7 (step S10, display step).

On the other hand, when the binning pixel number N in the image-capturing device 19 is larger than the predetermined threshold value (NO at step S4), the display switching portion 24 selects the "warning mode" (step S7). Then, the extracting portion 25 extracts the lesion part from the fluorescence image G2 sent from the display switching portion 24, creates the marker M showing the position of the extracted lesion part (step S8), and sends the created marker M to the superimposed-image generating portion 26. The superimposed-image generating portion 26 creates the superimposed image G in which the marker M is superimposed on the white-light image G1 (step S9) and outputs it to the display unit 7 (step S10, presenting step). If a region having gradation values equal to or greater than the prescribed threshold value does not exist in the fluorescence image G2, the superimposed-image generating portion 26 directly outputs the white-light image G1 to the display unit 7 as the superimposed image G (step S10).

Here, while the inserted portion 2 that is inserted in the body is being guided to the lesion part, since a lesion part does not exist in the observation field-of-view, the gradation values of the fluorescence image G2 become sufficiently low on the whole, and the binning pixel number N of the image-capturing device 19 is set to the upper limit. Therefore, a low-resolution fluorescence image G2 is generated. Instead of displaying this low-resolution fluorescence image G2 on the display unit 7, the clear white-light image G1 is displayed as the superimposed image G.

When a lesion part appears in the observation field-of-view, the representative value of the gradation values of the fluorescence image G2 rises. While the lesion part is being overviewed from a sufficiently distant position, the incident light level on the image-capturing device 19 is sufficiently small, and therefore, the binning pixel number N of the image-capturing device 19 set by the sensitivity adjusting portion 23 is sufficiently large, and the "warning mode" continues to be selected by the display switching portion 24. However, since the lesion part is extracted by the extracting portion 25, the marker M indicating this lesion part appears in the superimposed image G that is displayed on the display unit 7.

When the operator brings the distal end of the inserted portion 2 close to the position indicated by the marker M, the incident light level of fluorescence on the image-capturing device 19 increases, and the binning pixel number N of the image-capturing device 19 set by the sensitivity adjusting portion 23 decreases. Thus, when the distal end of the inserted portion 2 is sufficiently close to the lesion part, the binning pixel number N is equal to or less than the predetermined threshold, and the display switching portion 24 switches from the "warning mode" to the "normal mode". By doing so, the marker M is removed from the superimposed image G, and the fluorescence image G2 is displayed. The fluorescence image G2 displayed at this time is a high-resolution image acquired by the image-capturing device 19 using a sufficiently small binning pixel number N. Therefore, the operator can reliably and clearly recognize the lesion part in the superimposed image G.

In this way, with the fluoroscopy apparatus 1 according to this embodiment, by increasing the binning pixel number N of the image-capturing device 19 when the incident light level of fluorescence on the image-capturing device 19 is small, it is possible to reliably detect a lesion part existing in the observation field-of-view. In addition, the existence and position of the detected lesion part are shown by the marker M instead of the unclear fluorescence image G2, whose image quality has decreased due to the increase in the binning pixel number N. Thus, the operator can clearly recognize the existence and position of the lesion part. In addition, since a low-resolution fluorescence image is not superimposed on the white-light image G1, the operator can observe the clear white-light image G1 in the superimposed image G.

In this embodiment, the sensitivity adjusting portion 23 adjusts the image-capturing sensitivity of the image-capturing device 19 to fluorescence by adjusting the binning pixel number N of the image-capturing device 19; instead of this, however, the exposure time of the image-capturing device 19 or the gain coefficient of the signal from each pixel may be adjusted. In this case, the sensitivity adjusting portion 23 sends the exposure time or the gain coefficient to the display switching portion 24 instead of sending the binning pixel number N. Then, the display switching portion 24 switches the display mode depending on the exposure time or the gain coefficient.

The sensitivity threshold of the exposure time is set to, for example, 100 milliseconds. In this case, when the exposure time is less than or equal to 100 milliseconds (10 frames per second or more), the "normal mode" is selected, and when the exposure time is greater than 100 milliseconds (less than 10 frames per second), the "warning mode" is selected. The sensitivity threshold of the gain coefficient is set to, for example, 20 dB. In this case, when the gain coefficient is equal to or less than 20 dB (a gain coefficient equal to or less than a factor of 10), the "normal mode" is selected, and when the gain coefficient is larger than 20 dB (a gain coefficient larger than a factor of 10), the "warning mode" is selected.

In order to increase the sensitivity of the image-capturing device 19 to fluorescence, when the exposure time of the image-capturing device 19 is increased, image blurring occurs in the fluorescence image G2, and when the gain coefficient of the image-capturing device 19 is increased, the noise in the fluorescence image G2 increases. By displaying a marker M instead of such a low-quality fluorescence image G2, the existence and position of the lesion part can be clearly presented to the operator, and in addition, a clear white-light image G1 can be presented.

In this embodiment, the superimposed image G in which the fluorescence image G2 or the marker M is superimposed on the white-light image G1 by the superimposed-image generating portion 26 is displayed on the display unit 7; instead of this, however, the white-light image G1 and either the fluorescence image G2 or the marker M may be displayed on the display unit 7 side-by-side. Also, the white-light image G1 and the fluorescence image G2 may be displayed side-by-side in the "normal mode", and the white-light image G1 with the marker M superimposed thereon may be displayed in the "warning mode".

Figure 4:
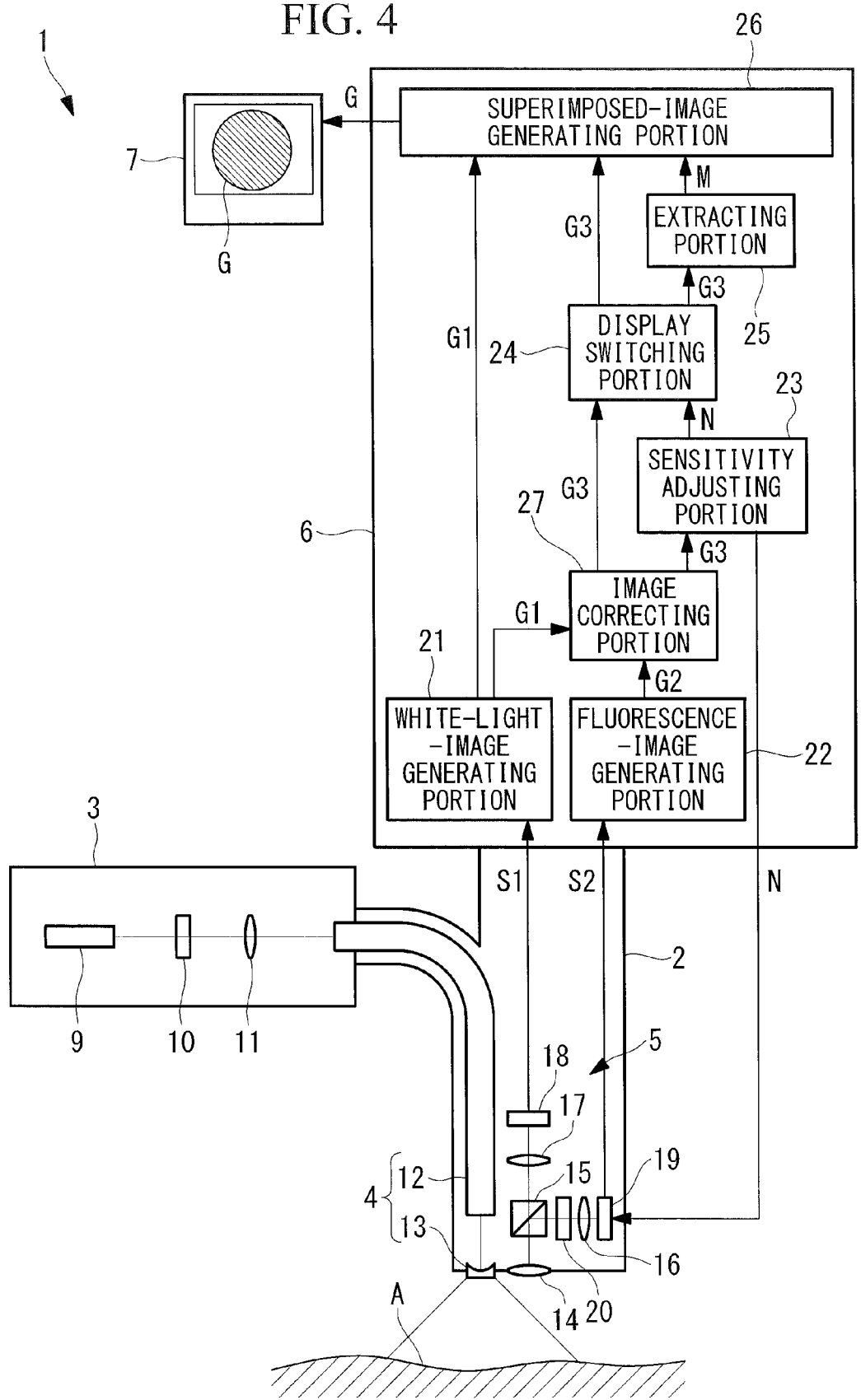
FIG. 4 is a diagram showing the overall structure of a modification of the fluoroscopy apparatus in FIG. 1.

As shown in FIG. 4, this embodiment may include an image correcting portion 27 that generates a corrected fluorescence image by dividing the fluorescence image G2 generated by the fluorescence-image generating portion 22 by the white-light image G1 generated by the white-light-image generating portion 21, and the sensitivity adjusting portion 23, the extracting portion 25, and the superimposed-image generating portion 26 may use the corrected fluorescence image G3 generated by the image correcting portion 27 for processing instead of the fluorescence image G2.

The intensity of the fluorescence or the reflected light captured by the image-capturing device 18 or 19 changes depending on the observation distance and observation angle. In the corrected fluorescence image G3, such changes in the fluorescence intensity depending on the observation distance and observation angle are eliminated. In other words, the gradation values of the corrected fluorescence image G3 faithfully reflect the actual intensity distribution of the fluorescence in the subject A. Therefore, by using the corrected fluorescence image G3, the setting of the binning pixel number N by the sensitivity adjusting portion 23 and the extraction of the lesion part by the extracting portion 25 can be performed more reliably.

In this embodiment, as the procedure for notifying the operator of the existence of a lesion part in the fluorescence image G2 in the "warning mode", use of the marker M displayed in the superimposed image G has been assumed; instead of this, however, a sound may be output. With this approach too, the operator can clearly recognize the existence of a lesion part in the field of view currently being observed.

In this embodiment, although an endoscope has been illustrated as an example of a fluoroscopy apparatus, the form of the fluoroscopy apparatus is not limited thereto; for example, an optical microscope configuration is also possible.

An invention according to the following observation method is derived from the above-described embodiment.

Another aspect of the present invention is an observation method using a fluoroscopy apparatus equipped with an excitation light source that radiates excitation light onto a subject; a fluorescence-image acquiring portion provided with an image-capturing device that acquires a fluorescence image by capturing fluorescence generated in the subject by irradiating the subject with the excitation light from the excitation light source; a sensitivity adjusting portion that sets a sensitivity of the image-capturing device to the fluorescence on the basis of a gradation value of the fluorescence image acquired by the image-capturing device; a notifying portion that extracts a region having a gradation value higher than a predetermined gradation threshold value from the fluorescence image acquired by the image-capturing device and that presents information showing the existence of the extracted region to an operator; a display unit that displays the fluorescence image acquired by the image-capturing device; and a display switching portion that displays on the display unit the fluorescence image acquired by the image-capturing device when the sensitivity set in the image-capturing device by the sensitivity adjusting portion is equal to or less than a predetermined threshold and that presents the information using the notifying portion when the sensitivity is greater than the predetermined threshold, the observation method including a step of taking an overview of the subject; and a step of bringing the image-capturing device close to the observation field-of-view in the overview step when the information is presented using the notifying portion in the overview step.

With this observation method, an observation field-of-view containing a lesion part is sought by taking an overview of the subject, and when an observation field-of-view containing a lesion part is found, that observation field-of-view is observed in a close-up, magnified manner. Thus, when taking an overview of the lesion part, the lesion part is reliably detected by making the sensitivity of the image-capturing device high, and the existence of the lesion part is notified to the operator by means of information using the notifying portion. Thus, the image-capturing device becomes close to the lesion part, thus making the incident light level of fluorescence on the image-capturing device sufficiently high, and when a high-quality fluorescence image is acquired by the image-capturing device at low sensitivity, the fluorescence image is presented on the display unit by the operation of the display switching portion. By doing so, the existence of the lesion part in the observation field-of-view can be reliably and clearly recognized by the operator.

REFERENCE SIGNS LIST 1 fluoroscopy apparatus
2 inserted portion
3 light source (excitation light source, illumination light source)

4 illumination unit
5 image-capturing unit
6 image processing unit
7 display unit
18 image-capturing device (fluorescence-image acquisition portion)
19 image-capturing device (reference-image acquisition portion)
21 white-light-image generating portion
22 fluorescence-image generating portion
23 sensitivity adjusting portion
24 display switching portion
25 extracting portion (notifying portion)
26 superimposed-image generating portion
27 image correcting portion
A subject
M marker
G superimposed image

The invention claimed is:

1. A fluoroscopy apparatus comprising:
an excitation light source configured to radiate excitation light onto a subject;
a fluorescence-image acquisition sensor configured to acquire a fluorescence image by capturing fluorescence generated in the subject by irradiating the subject with the excitation light from the excitation light source; and
a processor configured to:
calculate a gradation value of the fluorescence image acquired by the fluorescence-image acquisition sensor;
set a sensitivity of the fluorescence-image acquisition sensor to the fluorescence on the basis of the gradation value;
extract a region having a gradation value higher than a predetermined gradation threshold value from the fluorescence image acquired by the fluorescence-image acquisition sensor with the set sensitivity;
generate a marker showing the existence of the region;
control a display to display the marker when the set sensitivity is greater than a predetermined sensitivity threshold; and
control the display to display the fluorescence image acquired by the fluorescence-image acquisition sensor instead of the marker when the set sensitivity is equal to or less than the predetermined sensitivity threshold.

2. The fluoroscopy apparatus according to claim 1, further comprising:
an illumination light source configured to radiate illumination light onto the subject; and
a reference-image acquisition sensor configured to acquire a reference image by capturing reflected light reflected from the subject when the illumination light from the illumination light source is radiated onto the subject,
wherein the marker shows the position of the region, and
wherein the processor is configured to:
control the display to display the fluorescence image in a superimposed manner on the reference image acquired by the reference-image acquisition sensor when the set sensitivity is equal to or less than the predetermined sensitivity threshold; and
control the display to display the marker in a superimposed manner on the reference image when the set sensitivity is greater than the predetermined sensitivity threshold.

3. The fluoroscopy apparatus according to claim 2,
wherein the processor is further configured to:
generate a corrected fluorescence image in which the fluorescence image is corrected by dividing the fluorescence image using the reference image; and
extract the region from the corrected fluorescence image.

4. A fluoroscopy apparatus operating method comprising:
calculating a gradation value of a fluorescence image of a subject acquired by a fluorescence-image acquisition sensor;
setting a sensitivity of the fluorescence-image acquisition sensor to the fluorescence on the basis of the gradation value;
extracting a region having a gradation value higher than a predetermined gradation threshold value from the fluorescence image acquired by the fluorescence-image acquisition sensor with the set sensitivity;
generating a marker showing the existence of the region;
controlling a display to display the marker when the sensitivity is greater than a predetermined sensitivity threshold; and
controlling the display to display the fluorescence image acquired by the fluorescence-image acquisition sensor instead of the marker when the set sensitivity of the fluorescence-image acquisition sensor is equal to or less than the predetermined sensitivity threshold.

* * * * *